United States Patent [19]

Kesting

[11] 4,333,972

[45] Jun. 8, 1982

[54] HIGHLY ANISOTROPIC MEMBRANES

[75] Inventor: Robert E. Kesting, Irvine, Calif.

[73] Assignee: Puropore, Inc., Tustin, Calif.

[21] Appl. No.: 162,679

[22] Filed: Jun. 25, 1980

[51] Int. Cl.$^3$ ............................................. B05D 5/00
[52] U.S. Cl. .................................... 427/244; 427/246
[58] Field of Search ......................... 264/41, DIG. 48; 210/500.2; 427/244, 246

[56] References Cited

U.S. PATENT DOCUMENTS

| | | | |
|---|---|---|---|
| 3,792,135 | 2/1974 | Brown et al. ................ | 210/500.2 X |
| 3,884,801 | 5/1975 | Kesting ....................... | 210/500.2 X |
| 4,035,459 | 7/1977 | Kesting ....................... | 210/500.2 X |

Primary Examiner—Evan K. Lawrence
Attorney, Agent, or Firm—Knobbe, Martens

[57] ABSTRACT

The discovery that highly anisotropic membranes, e.g. with a degree of anisotropy of five can for the very first time be produced by the dry phase inversion process by a very specific combination of polymers, solvent and non-solvent, optionally along with plasticizers and modifiers, all of which separately are known in membrane technology, the polymers consisting essentially of cellulose nitrate and cellulose nitrate-cellulose acetate mixed ester polymers, the solvent being methyl formate, propylene oxide, or mixtures thereof, and the non-solvents being isopropyl alcohol, t-butyl alcohol or mixtures thereof, is disclosed.

8 Claims, 9 Drawing Figures

AIR FLOW RATE
($\ell$ min.$^{-1}$ cm$^{-2}$)

FIG. 3 WATER FLOW RATE (ml min.⁻¹ cm⁻²)

WATER FLOW RATE
(ml min.$^{-1}$ cm$^{-2}$)

BUBBLE POINT OF
WATER-WET MEMBRANES
(psig)

HIGHLY ANISOTROPIC MEMBRANES

TECHNICAL FIELD

Synthetic polymeric membranes have been described, the background and development reported, and the theory of formation described, Kesting, R. E., SYNTHETIC POLYMERIC MEMBRANES, McGraw-Hill Books Company, New York, 1971. The dry phase inversion process for forming membranes generally is described by Kesting, ibid. The publications and patents cited herein are incorporated by reference in lieu of a verbatim repetition of the pertinent discussions therein.

The present invention is a step in the evolution of the colloidal morphology of phase inversion membranes, which conceptually began with dense polymer films and diverged into two principal branches of skinned and skinless membranes, as illustrated in Table 1.

TABLE 1

Evolution of the Morphology
of Phase Inversion Membranes
Dense Polymer Films ~ 1850

| SKINNED MEMBRANES | SKINLESS MEMBRANES |
|---|---|
| Integrally skinned ultragels (1960) | Slightly anisotropic microgels (1907) |
| Nonintegrally skinned microgels (1965) | Moderately anisotropic microgels (1977) |
| Integrally skinned microgels (1970) | Highly anisotropic microgels (1980) |

The first membranes history reports were largely cellulosic. Collodion (nitrocellulose) membranes were reported by A. Fick, *Ann. Physik Chem.*, 94:59 (1855). The first major step from these initial studies was the development by Bechhold (H. Bechhold, *Z. Physik. Chem.*, 60:257 [1907]) early in this century of membranes of graded porosity. The second major step in the development of membranes was the development of integrally skinned ultragels by Loeb and Sourirajan (S. Loeb and S. Sourirajan, UCLA *Rept.* 60—60, 1960). These asymmetric or skinned membranes, comprising a body of open pore membrane structure with a very thin dense skin layer found immediate application in reverse osmosis technology. The third major breakthrough in membrane technology was the development in the middle 1960's of ultrathin composite membranes by Cadotte and Francis (U.S. Pat. No. 3,580,841, Cadotte, et al.; J. E. Cadotte, L. T. Rozelle, R. J. Petersen, and P. S. Francis, Water Transport Across Ultrathin Membranes of Mixed Cellulose Ester and Ether Derivatives, in MEMBRANES FROM CELLULOSE AND CELLULOSE DERIVATIVES, A. F. Turbak, Ed., John Wiley & Sons, Inc., 1970; P. S. Francis, et al., Fabrication and Evaluation of New Ultrathin Reverse Osmosis Membranes, Research and Development Progress Report No. 177, February 1966, United States Department of the Interior). The fourth major development was the fabrication of integrally skinned microgels, U.S. Pat. No. 3,884,801, R. E. Kesting. The present discovery and invention constitutes the fifth major advance in membrane technology.

Cellulose acetate is by far the most used polymer in the formation of microfiltration membranes, with other cellulose esters and mixed esters being widely used. Kesting, SYNTHETIC POLYMERIC MEMBRANES, supra, discusses at length cellulosic membranes generally and give numerous examples of cellulose acetate and mixed ester membranes. Reverse osmosis cellulose ester membranes formed by the dry phase inversion process are described in detail in U.S. Pat. No. 3,884,801, and hollow fiber cellulose ester membranes are disclosed in U.S. Pat. No. 4,035,459, Kesting, R. E., July 12, 1977. Cadotte et al., U.S. Pat. No. 3,580,841, May 25, 1971, list numerous membrane forming polymers including cellulose acetate, cellulose nitrate, and mixed cellulose esters.

Cellulose acetate membrane forming characteristics have been studied in detail, including extensive studies on plasticizers, solvents and non-solvents for use in forming cellulose acetate membranes. Kesting, for example, recognized the high solvating power of propylene oxide and methyl formate for cellulose acetate. These solvents, alone and in mixture, have been investigated. Kesting also reported the effectiveness of isopropyl alcohol and t-butyl alcohol as non-solvents in the formation of membranes from methyl formate and propylene oxide solutions of cellulose acetate (see, e.g., U.S. Pat. No. 4,035,459, R. E. Kesting, July 12, 1977).

Ohtani, et al., described the production of a microporous sheet produced from a casting solution of: nitrocellulose, 15 parts; methyl formate, 44 parts; ethanol, 33 parts; water, 7 parts; and polyoxyethylene octylphenyl ether, 1 part (U.S. Pat. No. 4,097,383, Sumio Ohtani, Nobsco Hiratsuka and Masaru Horiguchi, June 27, 1978).

Asymmetric membranes are quite well known, see e.g., U.S. Pat. Nos. 4,035,459 and 4,884,801 and are described by Brown et al. (U.S. Pat. No. 3,792,135, B. M. Brown and E. L. Ray, Feb. 12, 1974) as including a "skin" or "active layer" with the remainder of the membrane usually being very porous with increasing porosity occurring as one proceeds in the direction through the membrane away from the "active" layer or "skin". This definition of membrane "asymmetry" is generally accepted in membrane technology (see, e.g., U.S. Pat. No. 4,048,271, R. E. Kesting, Sept. 13, 1977; U.S. Pat. No. 3,884,801, R. E. Kesting, May 20, 1975; Kesting, SYNTHETIC POLYMERIC MEMBRANES, supra, pp. 141-152).

The term "anisotropy", and its derivatives, is not widely used in membrane technology because anisotropic membranes are not common, but when used the term generally refers to a gradation in pore size between one side of the membrane to the other more or less continuous, as distinct from a thin "skin" on a porous supporting membrane structure as in the asymmetric membranes previously referred to. In many instances, there is some anisotropy within the porous supporting membrane structure of skinned, "asymmetric" membranes but the degree of anisotropy, if any, is small and the effect of the anisotropy is negligible or non-existent. Anisotropic membranes, which may be either "skinned" or "unskinned", depending upon particular processing techniques, of poly(arylene oxide), polycarbonate, polyvinyl acetate, polyalkyl methacrylate, polysulfone, or monovinyl aromatic hydrocarbon polymers are reported by Shiro G. Kimura, U.S. Pat. No. 3,762,136, Oct. 2, 1973.

The "ideal" filter as an integral mat of progressively finer pores, highly anisotropic, has been conceptualized, U.S. Pat. No. 3,353,682, D. B. Pall et al., Nov. 21, 1967. Slight anisotropy is exhibited by the Millipore (Trademark) HA type cellulose ester membrane, having a degree of anisotropy (DA) of less than 2 and a small pore size of 0.45 μm, referred to as the "conventional"

membrane hereinafter. Moderate anisotropy is exhibited in the Millipore (Trademark) HC type cellulose ester membranes, having an anisotropy of 3:1 and a fine pore size of 0.7 μm. Until now, however, an "ideal" highly anisotropic microporous polymeric membrane has not been possible. In the following discussion, the "conventional" M/E, i.e., Millipore M/E Membranes, are used for comparing the unpredictable and unexpected advance represented by the membrane disclosed hereinafter known as a Tyrann (Trademark) M/E (mixed ester) membrane. Other membranes less related to the presently disclosed and claimed membranes are also compared.

This invention, in summary terms, in a step function discovery advancing the state of the membrane art to a point significantly beyond the known technology for producing highly anisotropic membranes. It came as a great surprise that a particular combination of polymer(s), solvent(s), and non-solvent(s) produced, by otherwise conventional processing, a membrane of much higher anisotropy than heretofore known and, more importantly, a membrane which exhibited many highly unexpected and significant advances in the art.

DISCLOSURE OF THE INVENTION

It has been discovered that there is a most unexpected synergism insofar as results in the casting according to known technology of a new combination of polymer, solvent, and non-solvent. Specifically, it has been discovered that there is a special synergism in the formation of microporous membranes from a casting solution consisting essentially of three basic components (plus, optionally, various modifiers which do not interfere with the membrane formation), namely: a membrane polymer which consists essentially of cellulose nitrate or cellulose nitrate-cellulose acetate mixed ester polymer; a solvent which consists essentially of methyl formate, propylene oxide or mixtures thereof; and a non-solvent consisting essentially of isopropyl alcohol, t-butyl alcohol or a mixture of these alcohols.

If has been discovered that membranes cast from the aforesaid synergistic casting solution have a higher anisotropy than previously attainable, i.e. considerably greater than 3:1 anisotropy being measured by the ratio of the average pore size on the large pore or open side of the membrane to the average pore size on the small pore or tight or closed side of the membrane. In particular, it has been discovered that membranes cast on flat substrates using otherwise standard techniques result in membranes having an anisotropy of at least about 3.5 or more and typically to have an anisotropy of 5. It is possible, according to the discovery of this invention, to produce membranes having an anisotropy of 5±1 to 1, i.e. generally in the range of 4:1 to 6:1, optimum presently being about 5:1. This is a new result, unpredicted and unpredictable from the prior art.

It has also been discovered that certain materials, e.g. polymers, solvents and non-solvents generally regarded in the prior art to be equivalent one to another, within classes, are not in fact equivalent and, in point of fact, most unexpected synergism occurs when a particular set of materials is combined into a casting composition and the casting composition is cast to form microporous polymeric membranes.

In addition to the discovery that highly anisotropic microporous membranes are formed synergistically from the aforementioned casting solutions, it has been discovered that membranes so formed exhibit most unexpected advantages over prior art membranes. For example, the inventive 0.45 μm Tyrann M/E membrane has flow rates and throughputs which are only very slightly lower than those through a considerable more open but only moderately anisotropic membrane, Type HC, which has a fine pore size of 0.7 μm.

Reinforcing fibers have been formed into membranes but are known to reduce the flow rate and throughput of the filter membranes. The inclusion of reinforcing fibers in membranes of the present invention, however, has little or no effect on flow rate or throughput.

It has also been discovered that the membranes of this invention exhibit superior and unexpected microfiltration characteristics which make them highly valuable in the counting and filtration of bacteria containing solutions. Unexpectedly more effective bacteria retention, reliable sterilization efficiency, and accurate bacteria counting, coupled with unpredictably increased flow rate and throughput are accomplished.

The membranes of the present invention exhibit a surprising increase in toughness and flexibility. Indeed, it is possible to crease most membranes formed according to this discovery and invention, in contrast to the rather fragile and brittle prior art mixed ester membranes.

It has further been discovered that membranes according to the present invention are more thermally stable than prior art cellulose membranes, exhibiting less shrinkage and more uniform shrinkage during autoclaving.

All of these discoveries, these unexpected and unpredictable advantages, the unexpected synergism which produces these unique highly anisotropic membranes, the synergistic solution and the membranes resulting from the synergism which has been discovered, individually and taken together as a whole constitute the subject matter which I claim as my invention.

DESCRIPTION OF THE PREFERRED EMBODIMENT

Figure 1:
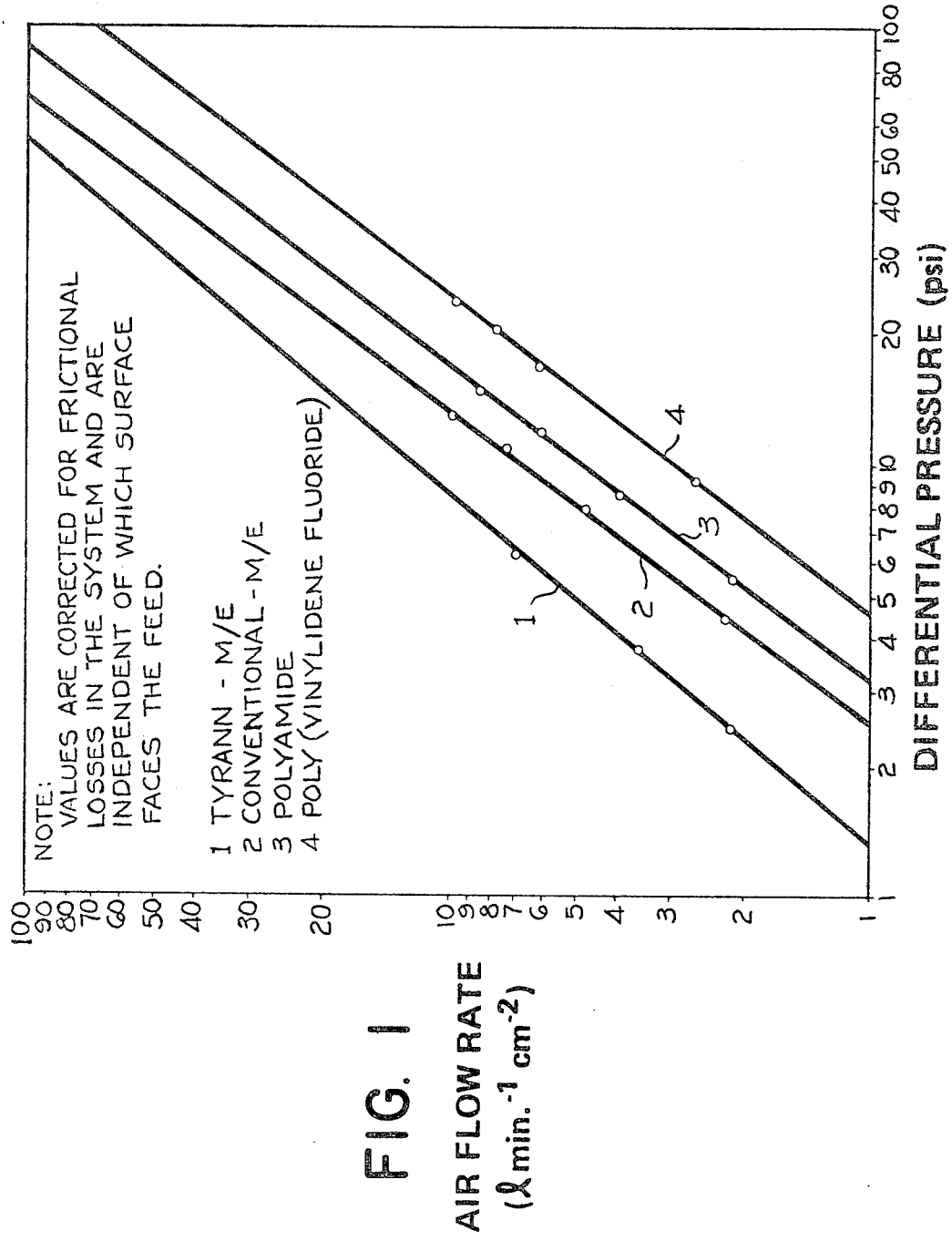
FIG. 1 graphically compares air flow rates of 0.45 μm Tyrann M/E membranes of this invention with conventional M/E and other membranes.

The following description and examples are given to describe and discuss and to exemplify my invention, and not as limitations thereupon except as expressly stated, and the scope of my invention as I conceive it is set forth in the claims appended hereto.

Materials: The present invention contemplates the use of three basic, essential classes of materials, polymers, solvents and non-solvents, and optionally includes the use of additional materials which do not significantly effect the membrane forming characteristics of the aforementioned materials.

Polymers: The only polymers known to be useful in the present invention are cellulose nitrate and cellulose acetate. Minor amounts of other polymers may, of course, be included if such addition does not destroy the synergism which permits and results in the formation of the highly anisotropic membranes of this invention. The preferred polymer is a mixed cellulose ester polymer consisting essentially of from about 85% to 90%, optimum now believed to be about 88%, cellulose nitrate with the balance of the polymer consisting essentially of cellulose acetate. Such cellulose nitrate-cellulose acetate mixed ester polymers may include from as much as 50% to as little as zero percent cellulose acetate and remain within the present invention, but the membranes of the invention will generally include no more than about 20% cellulose acetate, the balance consisting essentially of cellulose nitrate. Cellulose acetate may be omitted entirely; however, it has been discovered that it is much easier to form integral, uniform membranes from casting solutions which contain at least about 5% or more cellulose acetate and preferably in the 10% to 15% range of cellulose acetate.

Commercially available cellulose nitrate and cellulose acetate are quite suitable for use in this invention. There is some variation in results, and in processing details, depending upon the source and viscosity grade of cellulose ester, and some modest experimentation will be required to select the most easily handled polymers which give the best results. Other than some empirical results with specific grades of cellulose esters, no defined criteria have been established for pre-selecting cellulose esters.

Eastman (Trademark) cellulose acetates have been found to be quite satisfactory. Eastman E-394-60 cellulose acetate, for example, has proved to be quite useful in the present invention. Other cellulose acetates include Eastman E-432-130B, E-398-10, E-394-30, E-394-45, and E-400-25. Obviously, other sources of cellulose acetate may be used with equal or satisfactory results, the foregoing being merely exemplary. Cellulose acetates generally suitable for use in this invention are as identified and described in the Kirk-Othmer, ENCYCLOPEDIA OF CHEMICAL TECHNOLOGY, Second Edition, Vol. 4, article, "Cellulose Derivatives" p. 616, e.g. "Cellulose Acetate" pp. 632 et.seq.

Hercules (Trademark) cellulose nitrate has been found to be quite stuitable for use according to this invention. Hercules "RS" cellulose nitrate, for example, results in excellent quality membranes when incorporated in the synergistic casting solution and cast as membranes. Again, some viscosity grade selection may be made based on experience but cellulose nitrate from nearly any source may be used. Kirk-Othmer, supra at p. 625 et. seq., article "Cellulose Nitrate" describes cellulose nitrates suitable for use in this invention.

Generally, it presently appears that smaller pore sizes are more readily attainable with high molecular weight polymers; however, pore size is also dependent upon other factors, such as concentration of polymer in the casting solution, and preliminary testing of a given casting solution is required.

Mixed ester polymers are formed, most easily, simply by dissolving the desired ratios, by weight, cellulose acetate and cellulose nitrate into the solvent; however, no order of dissolution or method of forming mixed cellulose ester polymer casting solutions is critical to the present invention.

Solvent. Ordinarily, all solvents for cellulose nitrate and cellulose acetate have been generally regarded as equivalent one to another. While different solvating powers had been recognized and it was known that viscosity differed, for a given concentration, from solvent to solvent, no difference in kind of result obtained using various solvents was generally recognized and none of the specific selections of the prior art provided a foundation for predicting that one solvent, in a casting solution of a polymer and a non-solvent, would result in a highly anisotropic membrane as described hereinbefore.

It has been discovered, however, that only two known solvents are capable of co-acting synergistically to produce the highly unexpected and advantageous results previously mentioned. Thus, insofar as I presently know, the only solvents satisfactory for this invention consist essentially of methyl formate, propylene oxide or mixtures thereof. Of course, amounts of another solvent which did not destroy the unexpected synergism of the casting solution may be included, though such solvents would not seem to contribute to the invention and may be detrimental, especially if present in more than small percentages. Water may, optionally, be added as a co-solvent and is especially beneficial, in small amounts of under 10% of the total casting solution, when propylene oxide is the solvent. Though not fully understood or explored, it seems that water sometimes makes membrane formation easier and may moderately strengthen the membrane.

Non-Solvent. Alcohols, especially the highly volatile lower alcohols, have been known as non-solvents in membrane casting solutions. Ethyl alcohol, for example, was used by Sumio Ohtani et al., U.S. Pat. No. 4,097,383, in casting solutions of nitrocellulose and methyl formate. I have now discovered, however, that a unique and unexpected synergism occurs in the combination of a polymer as described in solution in methyl formate in a casting solution in which the non-solvent is isopropyl alcohol, t-butyl alcohol or mixtures of these alcohols. This synergism does not occur with ethyl alcohol nor does it occur, to the best of my knowledge, with any other non-solvents.

Casting Solutions. The casting solutions of this invention which exhibit the unexpected synergism consist essentially of a cellulose nitrate or cellulose nitrate-cellulose acetate mixed ester polymer dissolved in methyl formate or propylene oxide and isopropyl alcohol, t-butyl alcohol or a mixture of these alcohols as a non-solvent also dissolved in methyl formate.

No critical concentration ranges have been identified, except, of course, that the casting medium must be a solution, i.e., the polymer and the non-solvent must be in solution. The preferred ranges of the respective components are shown in the following table:

TABLE 2

| | Casting Solution Composition | |
|---|---|---|
| | General Range (Weight Percent) | Preferred Range (Weight Percent) |
| Solvent | 40% to 80% | 45% to 60% |
| Non-solvent | 20% to 60% | 40% to 55% |
| polymer | 0.1% to 10% | 1% to 5% |

Additional Constituents. It is common to add constituents to casting solutions which affect the ultimate membrane in one or more of its characteristics but which have little, and usually nothing, to do with the membrane formation per se. This practice is quite compatible with the present invention. For example, any non-volatile component which may desirably be incorporated in the membrane may be added to the casting solution or to the cast layer of solution. Biological agents, detergents, dyes, etc., for example, may be included in the membrane, all according to conventional membrane forming techniques. It has been found to be advantageous to add a small amount of glycerol as a plasticizer and wetting agent for the ultimate membrane, to increase the flexibility and ease of handling and storage of the present Tyrann M/E membranes. The glycerol is quite compatible with most uses of the membrane; however, in any application where a zero-extractable membrane is desired, it is possible to leach all of the glycerol from the membrane quickly with small amounts of leach water or solution. The present membrane is then left free of all extractable constituents. It is especially significant that there is no detergent present in the membrane, since detergents or wetting agents are not compatible with many applications of the membranes.

Reinforcing fibers. It is known to cast membranes over fibers or fabrics, woven or non-woven, to increase the strength of the membrane. In all such instances, the inclusion of a matrix of reinforcing fibers has resulted in a decrease, often a very dramatic decrease, in flow rate through the membrane. It has been discovered that reinforcing fibers can be included in the open pore portion of the present highly anisotropic membranes without significant reduction in either flow rate or throughput of the membrane. Any reinforcing fiber may be used. A non-woven polyester fabric is exemplary of the types of reinforcing which are suitable. In the example, the synergistic casting solution is cast over and flows through the fabric such that when the membrane is dried the fibers mainly are in the coarse pore section of the membrane generally adjacent the "input" or first side of the membrane, i.e. the bottom side as made. In its preferred form, the membrane of this invention comprises two generally well defined portions: a first portion adjacent the first (input or coarse pore) side of the membrane, and a second portion adjacent the second (output or fine pore) side of the membrane, the first portion having a graded but average pore size more than three times and usually at least about three and one-half times the pore size on the second side. The fibers are mainly in the first portion and do not effect, or have only an insubstantial effect upon, the flow rate capacity or the throughput capacity of the membrane.

Casting Technique. The membranes of this invention are cast using conventional casting equipment and conventional casting technique. As in all casting processes, there is some adjustment to be made in rate of casting, temperature, viscosity, rate of evaporation, rate of removal of solvent vapor, etc.; however, these are routine, largely empirical adjustments made in accordance with experience with a particular casting line. No non-routine adjustments need be made in the casting of membranes using the synergistic casting solution of this invention. The general casting techniques in the dry phase inversion method are described by in SYNTHETIC POLYMERIC MEMBRANES, Kesting, R. E., McGraw-Hill 1971 and in numerous prior publications and patents. In general, a typical casting machine will include a continuous belt of any desired width, e.g. up to 36 to 48 inches typically, mounted to travel a path extending of from 50 to 150 feet providing a smooth flat moving substrate upon which a layer of casting solution is spread using any suitable or desirable type of spreading mechanism. A doctor blade, wire wound rod or other spreader may be used, or the solution may simply be extruded uniformly from an elongate narrow nozzle onto the substrate. The substrate is usually enclosed wholly or partially and a conduit system is provided for removing solvent and non-solvent vapors as they evaporate from the layer of casting solution during membrane formation. A roller or other means for laying a reinforcing fiber layer is included in the instance where such fibers are formed into the membrane. Speed, temperature, air or gas flow, application rate and other controls common to such machinery, which per se is not part of this invention, are provided.

Exemplary Casting Solutions. The following solution compositions are given to exemplify, and not to limit or circumscribe, the casting solutions which have been discovered to exhibit the unexpected synergism when cast into microporous polymeric membranes by the dry phase inversion process.

EXAMPLE 1

| Solvent - Methyl Formate | 51.18 Parts |
|---|---|
| Non-Solvent - Isopropyl Alcohol | 45.72 Parts |
| Polymer - Cellulose Nitrate | 2.65 Parts |
| - Cellulose Acetate | 0.36 Parts |
| Glycerol | 0.09 Parts |

The casting solution was prepared by dissolving the polymer in the solvent, and then dissolving the other constituents into the resulting solution. The casting solution when cast into a thin film on a substrate and dried substantially to complete removal of the solvent and non-solvent forms an integral, flexible microporous membrane suitable for microfiltration, the characteristics of which are discussed in detail. The pore size formed was 2.5 $\mu$m on the first, course side and 0.45 $\mu$m on the second, closed or fine, side of the membrane.

EXAMPLE 2

| Solvent - Methyl Formate | 50.80 Parts |
|---|---|
| Non-Solvent - Isopropyl Alcohol | 45.4 Parts |
| Polymer - Cellulose Nitrate | 3.22 Parts |
| - Cellulose Acetate | 0.45 Parts |
| Glycerol | 0.11 Parts |

The casting solution was prepared by dissolving the polymer in the solvent, and then dissolving the other constituents into the resulting solution. The casting solution when cast into a thin film on a substrate and dried substantially to complete removal of the solvent and non-solvent forms an integral, flexible microporous membrane suitable for microfiltration, the characteristics of which are discussed in detail. The pore size formed was 4 μm on the first, course side and 0.8 μm on the second, closed or fine, side of the membrane.

EXAMPLE 3

| | |
|---|---|
| Solvent - Methyl formate | 54.4 Parts |
| Non-Solvent - Isopropyl Alcohol | 42.1 Parts |
| Polymer - Cellulose Nitrate | 2.82 Parts |
| Cellulose Acetate | .38 Parts |
| Glycerol | .36 Parts |

The casting solution was prepared by dissolving the polymer in the solvent, and then dissolving the other constituents into the resulting solution. The casting solution when cast into a thin film on a substrate and dried substantially to complete removal of the solvent and non-solvent forms an integral, flexible microporous membrane suitable for microfiltration, the characteristics of which are discussed in detail. The pore size formed was about 1 μm on the first, course side and 0.2 μm on the second, closed or fine, side of the membrane.

EXAMPLE 4

| | |
|---|---|
| Solvent - Propylene oxide | 49.3 Parts |
| Non-Solvent - Isopropyl Alcohol | 43.6 Parts |
| Polymer - Cellulose Nitrate | 3.52 Parts |
| Cellulose Acetate | .48 Parts |
| Water | 4.00 Parts |
| Glycerol | .40 Parts |

The casting solution was prepared by dissolving the polymer in the solvent, and then dissolving the other constituents into the resulting solution. The casting solution when cast into a thin film on a substrate and dried substantially to complete removal of the solvent and non-solvent forms an integral, flexible microporous membrane suitable for microfiltration, the characteristics of which are discussed in detail. The pore sizes were 0.5 μm and 0.1 μm on the respective sides of the membrane.

T-butyl alcohol or mixtures of t-butyl and isopropyl alcohol as the non-solvent give comparable results.

DISCUSSION

Towards the end of determining the most promising polymer system for development into a new class of microfiltration membranes, an experimental survey was conducted to establish the filtration characteristics, as well as the mechanical and thermal properties, of commercially available microfiltration membranes. To anticipate the survey results, which will themselves be found throughout the following discussion where comparisons between the various membrane types are appropriate, it was discovered that cellulose mixed ester M/E membranes generally exhibited filtration characteristics which are superior, and mechanical and thermal properties inferior, to those of noncellulosic microfilters. Because filtration characteristics were of paramount importance, the M/Es were chosen as the membrane polymers. At the same time it was felt that the poor flexibility and thermal properties exhibited by conventional M/E membranes were not intrinsic properties of the materials themselves.

At the inception of the project, therefore, the goals were to develop a new class of M/E membranes which would exhibit filtration characteristics which were superior to those of conventional M/E membranes, and which would simultaneously approach the desirable mechanical and thermal properties of their noncellulosic alternatives. This new class of M/E membranes has been designated Tyrann-M/E (Trademark).

FILTRATION CHARACTERISTICS

Air and Water Flow Rates

Figure 2:
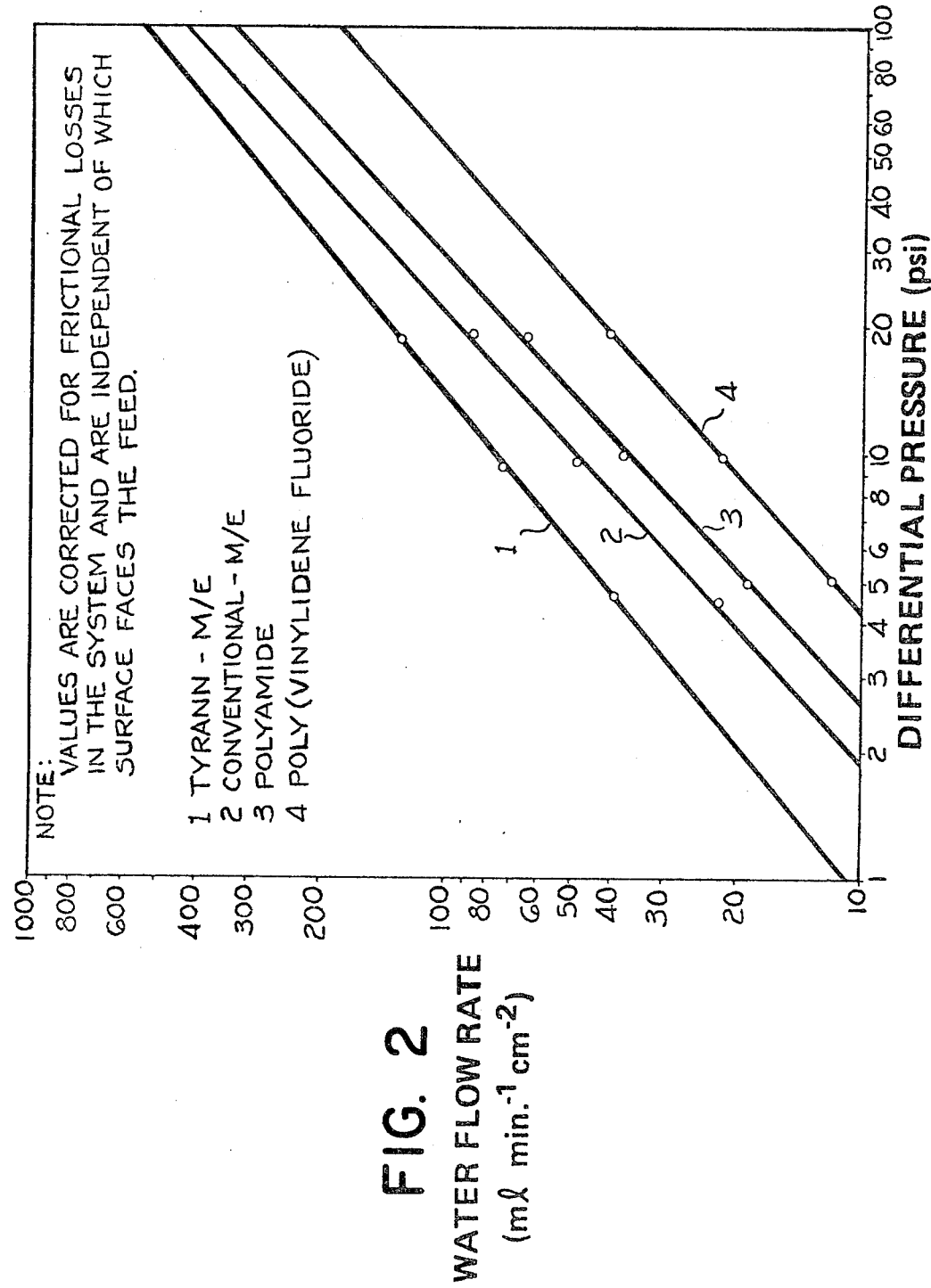
FIG. 2 graphically compares water flow rates of 0.45 μm Tyrann M/E membranes of this invention with conventional M/E and other membranes.

The air and water flow rates as functions of differential pressure (corrected for frictional losses in the test system) have been plotted for two noncellulosic 0.45 μm microfilters and for 0.45 μm Tyrann M/E and conventional M/E membranes, shown in the graphs of FIGS. 1 and 2. The flow rates for filtered air and water were found to be independent of which surface of the membranes faced the feed. In every case a linear relationship between pressure and flow rate was observed. The curves tend to parallel one another but at considerable displacements along the abscissa. This indicates that whereas all four types respond to pressure in approximately the same manner, there exist substantial differences between their permeabilities, with both M/E membranes exhibiting substantially greater flow rates than both of the noncellulosic types. The air flow rates for Tyrann-M/E are approximately twice those of conventional M/E membranes and three times those of polyamide membranes. The reasons for this are related to differences in morphology. The water flow rates for Tyrann-M/E membranes are also greater than those of both conventional M/E and noncellulosic membranes, see FIG. 2.

Typically, the water permeates Tyrann-M/E membranes at least 50% more rapidly than it does conventional M/E membranes and more than twice the rate of which it permeates the noncellulosic membranes. Although both air and water flow rates for the conventional M/E membranes are consistent with their published values, the claims that the two noncellulosic types "exhibit flow rates comparable to those of cellulosic membranes" are only valid for membranes with pores $\leq 0.2$ μm. The air and water flow rates for various 0.2, 0.45 and 0.8 μm membranes at 10 psid (corr.) are found in Table 3.

TABLE 3

Air and Water* Permeabilities and Filtration Capacities** of Various Microfiltration Membranes

| Membrane Type Pore Size-Class | | Bubble Point (psi) | Air Permeability ($1\ min^{-1}\ cm^{-2}$) | * | Water Permeability ($ml\ min^{-1}\ cm^{-2}$) | * | Filtration Capacity (Throughput)** |
|---|---|---|---|---|---|---|---|
| 0.2μm | Tyrann-M/E  (a) | 59.3 | 6.28 | 2.75 | 39.6 | 2.54 | 4.40 |
| | Con.-M/E    (b) | 45.9 | 2.28 | 1.00 | 15.6 | 1.00 | 1.00 |
| | Polyamide   (c) | 57.4 | 2.08 | 0.91 | 16.0 | 1.02 | 1.07 |
| | PVF         (d) | 53.0 | 1.37 | 0.60 | 7.34 | 0.47 | 0.67 |
| 0.45μm | Tyrann-M/E | 35 | 12.3 | 1.82 | 76.3 | 1.55 | 2.14 |

TABLE 3-continued

Air and Water* Permeabilities and Filtration Capacities** of Various Microfiltration Membranes

| Membrane Type Pore Size-Class | | Bubble Point (psi) | Air Permeability ($1\ min^{-1}\ cm^{-2}$) | * | Water Permeability ($ml\ min^{-1}\ cm^{-2}$) | * | Filtration Capacity (Throughput)** |
|---|---|---|---|---|---|---|---|
| | Con.-M/E | $32_i$–$40_f^+$ | 6.74 | 1.00 | 49.1 | 1.00 | 1.00 |
| | Polyamide | 34 | 4.92 | 0.73 | 36.0 | 0.73 | 0.50 |
| | PVF | $30.3_i$–$34.3_f^+$ | 2.92 | 0.43 | 22.2 | 0.45 | 0.34 |
| 0.8μm | Tyrann-M/E | 16 | 40.4 | 1.64 | 230 | 1.95 | 1.50 |
| | Con.-M/E | 15.6 | 24.5 | 1.00 | 118 | 1.00 | 1.00 |

*Normalized relative to the value for conventional-M/E
**Normalized relative to the values for conventional-M/E after 80% flow decay
+bubble points changed with duration of immersion: i = initial value, f = final value
(a) Tyrann (Trademark) cellulose mixed ester membranes of this invention.
(b) "Conventional" Millipore (Trademark) Type HA cellulose membranes.
(c) Prior art polyamide membranes, Pall (Trademark) Ultrapore.
(d) Prior art Millipore (Trademark) Duropore poly(vinylidene fluoride) membranes.

Flow Decay

Figure 3:
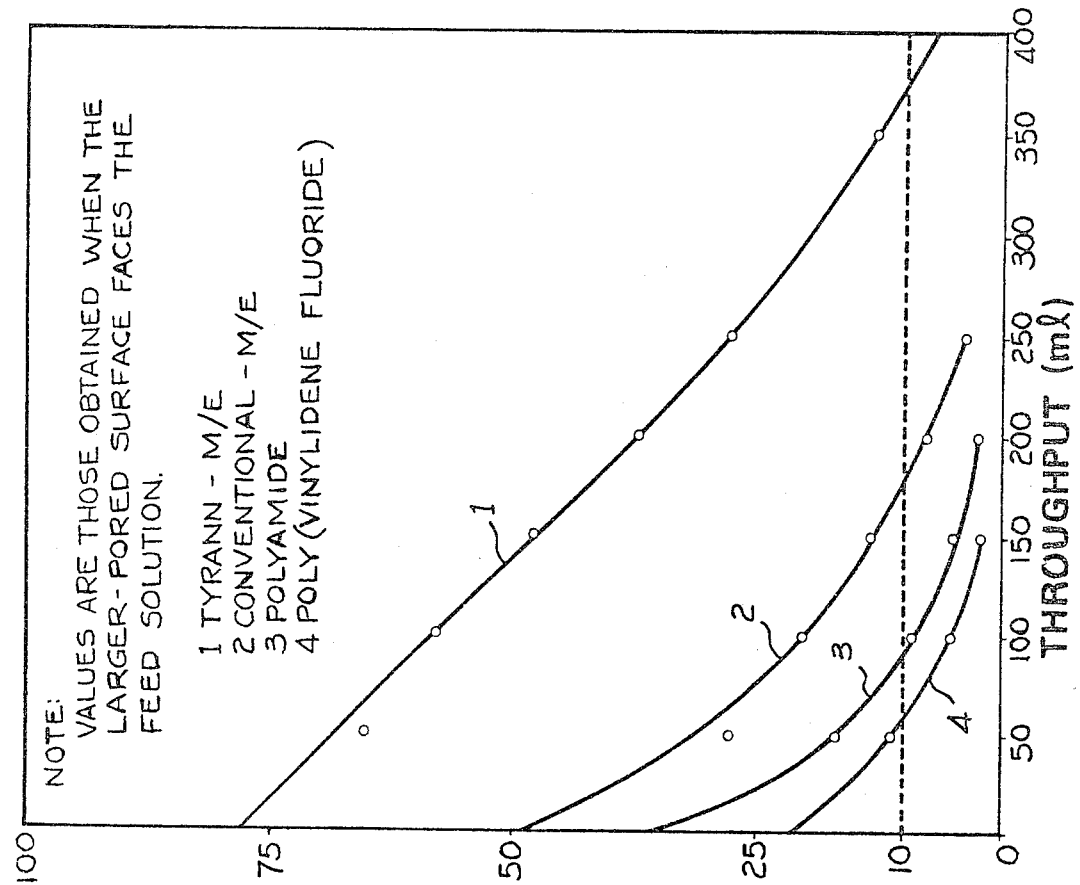
FIG. 3 graphically compares flow decay rates of 0.45 μm Tyrann M/E membranes of this invention with conventional M/E and other membranes.

One of the most important properties of a filter is its direct holding capacity, which affects throughput. This refers to the size of a batch of fluid which may be processed before a membrane becomes plugged by filtered particles thereby terminating or severely diminishing fluid flow. A convenient test of a membrane's filtration capacity is its performance on a flow decay experiment in which the product flow rate or permeability is plotted versus incremental volumes of filtrate, see FIGS. 3 and 4. The solute in this instance was Triton X-400. Since such tests are poorly reproducible in the absolute sense, they are most effectively carried out relative to the performance of a standard membrane exposed to the same solution at the same time. The reproducibility of these relative values is acceptable and shows that Tyrann-M/E has approximately one and one-half to two times the filtration capacity of the conventional M/E membrane which is itself superior to both noncellulosic membranes. Relative throughput were determined at the point where the permeabilities have decreased to twenty percent of that of the conventional M/E value. This is the point at which good standard practice requires that the conventional M/E membranes be changed. Both M/E membranes maintain their positions relative to those of the noncellulosic membranes throughput the test, see FIG. 3. Furthermore, the throughput advantage of Tyrann-M/E relative to other microfiltration membranes holds true over the entire range of pore sizes, see Table 3.

Figure 4:
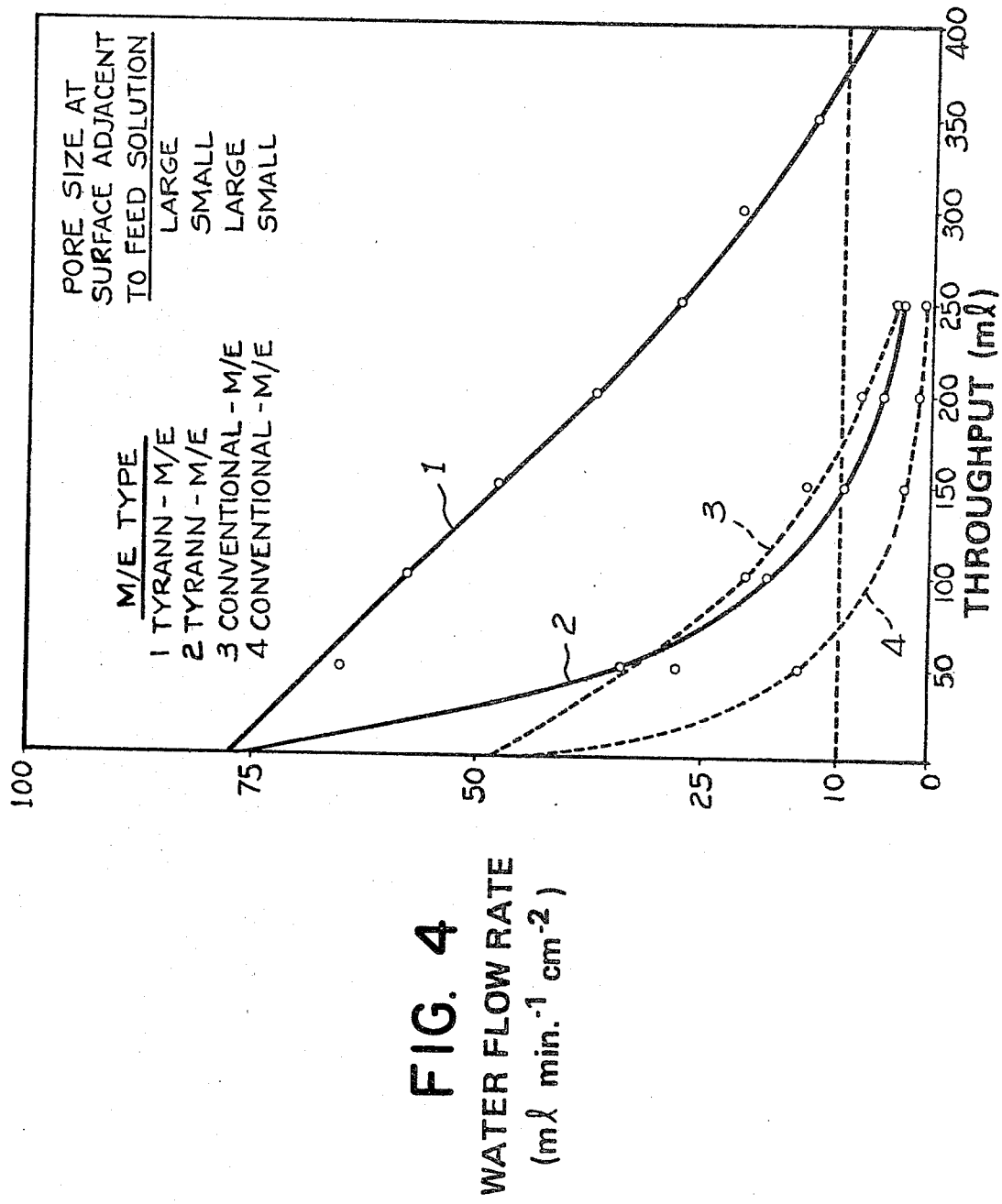
FIG. 4 graphically compares the effect of anisotropy upon flow decay rates of 0.45 μm Tyrann M/E membranes of this invention with conventional M/E and other membranes.

The effect of anisotropy upon the permeability and throughput of "course" and "fine" surfaces of conventional and Tyrann-M/E membranes is depicted in FIG. 4. It is apparent that throughputs are maximized by positioning the membranes so that the surface with the course, larger pores faces the incoming feed solutions. When this is done, the throughput of Tyrann-M/E is much greater than that of both conventional M/E and, of course, the noncellulosic membranes as well. However, throughput is greatly diminished when the fine pored surface is in contact with the feed, although it is still roughly equivalent to that for the larger pored surface of the conventional M/E membranes.

Bacteria Retention

Inasmuch as the raison d'être for microfiltration membranes is their ability to sterilize fluids by interdicting the flow of bacteria and other microbes via sieving and absorptive sequestration, bacterial challenges remain the crucially important test of the efficacy of microfiltration membrane. All of the 0.45 μm Tyrann-M/E membranes repeatedly sustained challenges of $10^3$, $10^5$, $10^7$, $10^9$/bacteria/$cm^2$ (*Serratia marcescens*) at 30 psid. The test procedure involved culturing of the Bacto-Peptone (B118) broth filtrate for 72 hours at 37° C. (3). The passage of even a single bacterium is sufficient to effect turbidity in the filtrate and constitutes a failure. The 0.2 μm Tyrann-M/E membranes, on the other hand, were challenged with $10^9$ bacteria/$cm^2$ (*Psuedomonas diminuta*). Although bacteria penetrated out of 3 samples of the conventional membranes, no bacterial penetration occurred through any of the Tyrann-M/E membranes of this invention. Bubble points were taken before sterilization and after completion of the challenge tests, see Table 4. The substantial increases in bubble point after undergoing high level bacterial challenge are believed to be the result of pore size reduction as a result of fouling by bacteria. It is significant that the conventional M/E membranes were plugged more readily than the Tyrann-M/E types. Retention tests were also carried out utilizing 0.50 μm monodisperse polystyrene latex spheres. Although some penetration of the surface layer of cells by the latex spheres was apparent in the case of both conventional M/E and Tyrann-M/E membranes, nevertheless, no beads were apparent beyond a depth of approximately 20 μm from the feed surface. However, it cannot be unequivocally stated that no penetration of latex spheres occurred because of the presence of occasional bead-like structures of the same size within the virgin membrane matrix. For this reason the bacterial retention test is considered more meaningful.

TABLE 4

Bacterial Retention at Various Challenge Levels for 0.2 and 0.45μm Tyrann-M/E and Conventional M/E Membranes

| Membrane | Initial Bubble Point (psi) | Challenge Level (CFU/47mm disc) | | | Final Bubble Point (psi) | 72 hr. Results* | | |
|---|---|---|---|---|---|---|---|---|
| | | 1st | 2nd | 3rd | | 1st | 2nd | 3rd |
| 0.45μm Tyrann-M/E (Lot A 00780) | 31.0 | $2.58 \times 10^7$ | $5.43 \times 10^7$ | $6.9 \times 10^7$ | 34.7 | — | — | — |
| | 31.2 | $2.58 \times 10^7$ | $5.43 \times 10^7$ | $6.9 \times 10^7$ | 36.3 | — | — | — |
| | 30.8 | $2.58 \times 10^7$ | $5.43 \times 10^7$ | $6.9 \times 10^7$ | 40.5 | — | — | — |

TABLE 4-continued

Bacterial Retention at Various Challenge Levels for 0.2 and 0.45μm Tyrann-M/E and Conventional M/E Membranes

| Membrane | Initial Bubble Point (psi) | Challenge Level (CFU/47mm disc) | | | Final Bubble Point (psi) | 72 hr. Results* | | |
|---|---|---|---|---|---|---|---|---|
| | | 1st | 2nd | 3rd | | 1st | 2nd | 3rd |
| 0.45μm Conventional M/E (Lot 191268) | 30.3 | 2.58 × 10⁷ | 5.43 × 10⁷ | 6.9 × 10⁷ | 53.5 | — | — | — |
| | 29.8 | 2.58 × 10⁷ | 5.43 × 10⁷ | 6.9 × 10⁷ | 42.5 | — | — | — |
| | 29.8 | 2.58 × 10⁷ | 5.43 × 10⁷ | 6.9 × 10⁷ | 46.2 | — | — | — |
| Tyrann-M/E | 30.1 | 2.46 × 10⁹ | 1.23 × 10¹⁰ | — | 48.0 | — | — | |
| | 31.0 | 2.46 × 10⁹ | 1.23 × 10¹⁰ | — | 53.6 | — | — | |
| | 30.6 | 2.46 × 10⁹ | 1.23 × 10¹⁰ | — | >60 | — | — | |
| Conventional M/E | 30.5 | 2.1 × 10⁹ | 1.05 × 10¹⁰ | — | 53.8 | — | — | |
| | 30.3 | 2.1 × 10⁹ | 1.05 × 10¹⁰ | — | 37.3 | — | +** | |
| | 39.6 | 2.1 × 10⁹ | 1.05 × 10¹⁰ | — | 54.7 | — | — | |
| 0.2μm Tyrann-M/E (Lot A03680) | 53.0 | 4.62 × 10⁸ | 9.24 × 10⁸ | 1.34 × 10⁹ | >70 | — | — | — |
| | 48.5 | 4.62 × 10⁸ | 9.24 × 10⁸ | 1.34 × 10⁹ | 69 | — | — | — |
| | 48.5 | 4.62 × 10⁸ | 9.24 × 10⁸ | 1.34 × 10⁹ | 57.4 | — | — | — |
| 0.2μm Conventional M/E (Lot C8H59206D) | 53.8 | 1.98 × 10⁸ | 1.97 × 10⁹ | 2.95 × 10⁹ | >70 | — | — | — |
| | 51.8 | 1.98 × 10⁸ | 1.97 × 10⁹ | 2.95 × 10⁹ | >70 | — | — | — |
| | 53.6 | 7.44 × 10⁸ | 1.49 × 10⁹ | 2.23 × 10⁹ | 36 | + | — | — |

*— = passed test; + = failed test
**This is considered a questionable failure because the pressure was increased to 40 psi after the membrane plugged at 30 psi.

Bacterial Recovery

The initial application of 0.45 μm Tyrann-M/E will be bacteria recovery in water analyses by the standard fecal coliform membrane filter procedure (4). Comparisons were made with respect to the recovery of *Escherichia coli* for both agar spread plates and conventional 0.45 μm M/E membranes, see Table 5. Whereas the Millipore HA M/E membranes recovered 71% of the bacteria indicated by the agar standard, Tyrann-M/E membranes recovered 96%. This difference is significant and may be related to a more efficient "cradling" of the bacteria by the highly anisotropic Tyrann M/E membrane. In fact, the course pores found (by SEM) in the surface of the Tyrann-M/E membrane which is exposed to the feed correspond to the previously established optimum values in a study in which it was also determined that the size of these pores is the primary determinant of fecal coliform growth on a membrane filter (5). An additional advantage of Tyrann-M/E is its lighter background color in the M-FC medium and the absence of interference from gridded areas with colony growth.

TABLE 5

Comparison of E Coli Recovery on Agar Spread Plates With Recoveries On Various 0.45 μm M/E Membranes

| Membrane | CFU* Agar | CFU Membrane | CFU Membrane/ CFU Agar × 100 (%) |
|---|---|---|---|
| Tyrann- | 46 | 41 | 96 |
| | 44 | 44 | |
| | 45 Avg. | 46 | |
| | | 37 | |
| | | 48 | |
| | | 43.2 Avg. | |
| Conventional- | 56 | 43 | 70.8 |
| | 58 | 35 | |
| | 57 Avg. | 45 | |
| | | 42 | |
| | | 37 | |
| | | 40.4 Avg. | |

*CFU = Colony forming unit.

Bubble Point Constancy

Although the exact relationship between the bubble point and the "pore size" of a microfiltration membrane is a matter of dispute (6–9), nevertheless, it remains the quickest and most convenient means for demonstrating the continuing integrity of a membrane filtration system.

Figure 5:
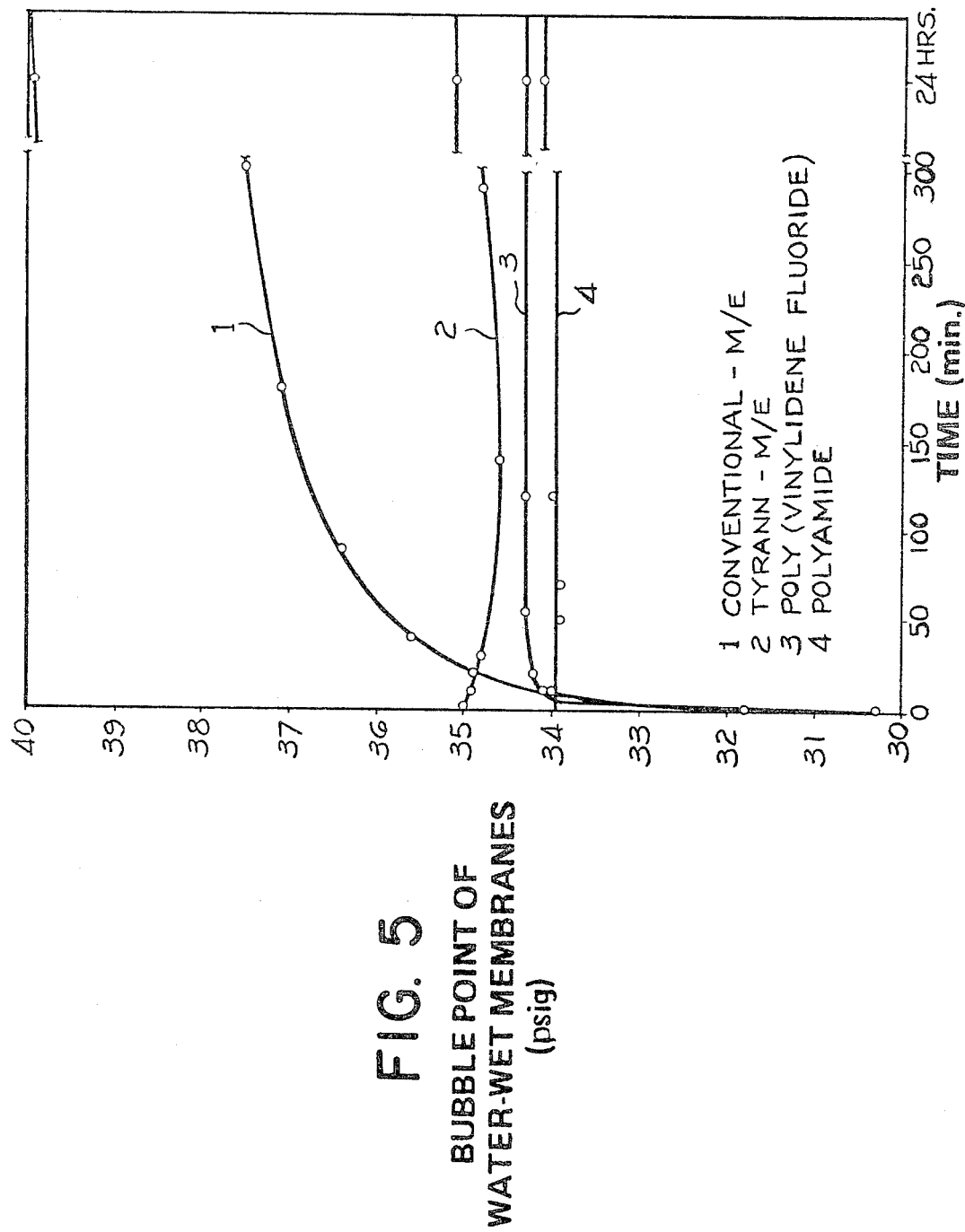
FIG. 5 graphically compares bubble point vs. duration of immersion for 0.45 μm membranes of this invention with conventional M/E and other membranes.

It is consequently important that the bubble point be both reproducible (within a given range) and constant. It was, therefore, of considerable interest to discover that the bubble points of both conventional M/E and poly(vinylidene fluoride) membranes increased with immersion time in deionized water whereas those of Tyrann-M/E and polyamide remained constant, see FIG. 5.

Some believe that the increase in the bubble point with time of the conventional M/E membranes is attributable to progressive leaching of the wetting agent. However, the poly(vinylidene fluoride) membrane does not contain an extraneous wetting agent and yet experiences the same behavior. Furthermore, the phenomenon is reversible, i.e. when the conventional M/E membrane is removed from water and allowed to dry before reimmersion in fresh water, the bubble point reverts back to the lowest value and once again progressively increases with increasing immersion time. These results are consistent with a reversible swelling (surface swelling would suffice) of conventional M/E and poly(vinylidene fluoride) membranes. The bubble points apparently increase with immersion time because the cell walls imbibe water and occupy progressively more space, thereby occluding a portion of the pore area which was previously available for air passage. Inasmuch as the membrane polymers in Tyrann-M/E are essentially the same as those found in conventional M/E membranes, any differences in behavior between the two are the results either of differences in microstructure and/or the type or concentration of additives such as wetting agents. Whereas conventional M/E membranes contain somewhat less than five percent (by weight of polymer) of a polyoxyethyleneoctylphenol, (Triton X-100, Trademark), Tyrann-M/E contains only glycerol as a wetting agent. The persistence of such frank wetting agents even after aqueous leaching is well known and, in fact, has been utilized to form liquid membranes at the interface between reverse osmosis membranes and a saline solution interface by intermittent addition of surfactants to a saline feed solution (10,11). Glycerol, on the other hand, is not only unobjectionable from a toxicity standpoint, but is rapidly and quantitatively removed by aqueous extraction.

Glycerol Extraction

Figure 6:
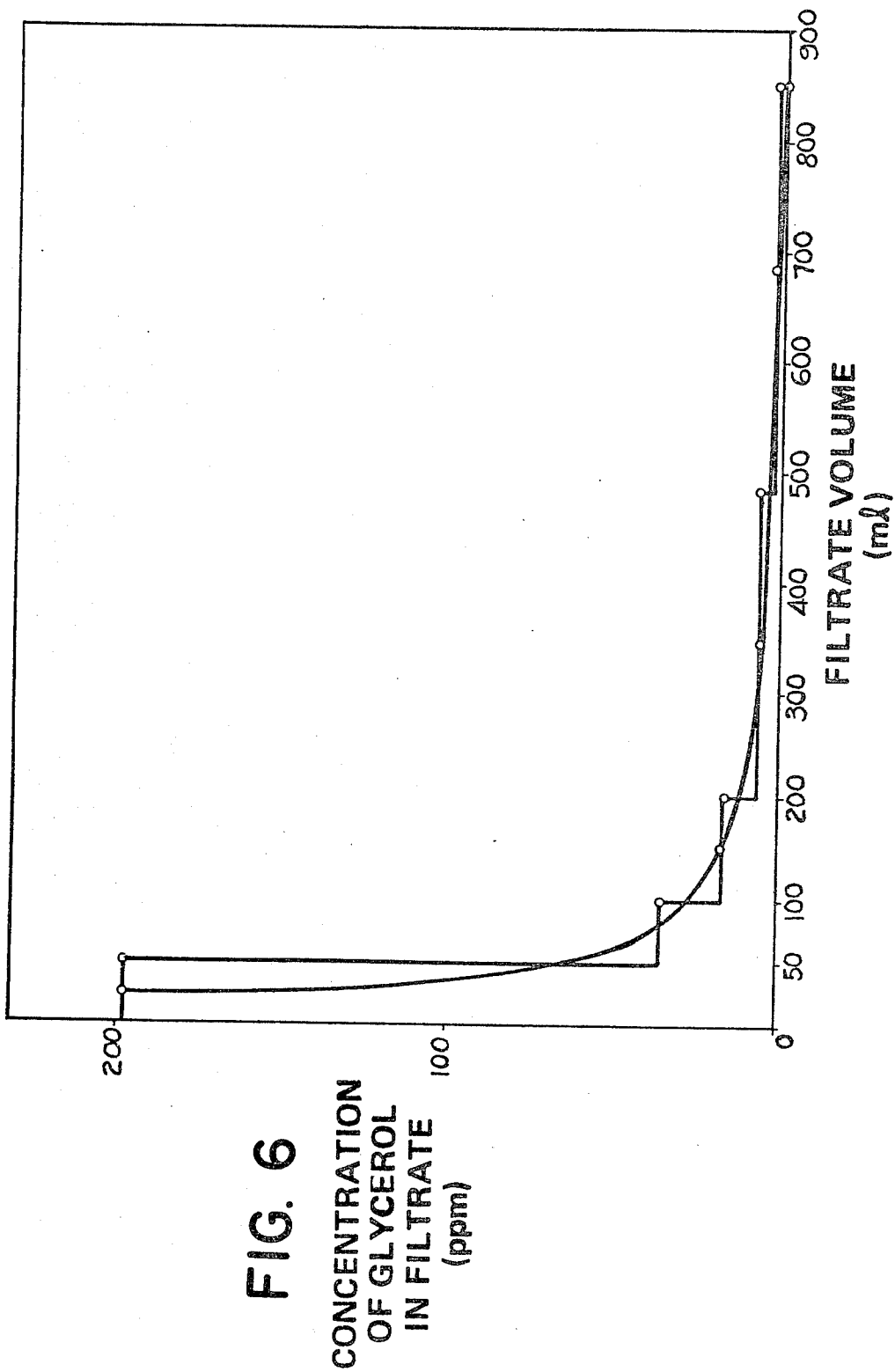
FIG. 6 is a glycerol extraction rate curve for 0.45 μm Tyrann M/E membranes of this invention.

Although glycerol has been employed as a wetting agent and plasticizer from the earliest days of cellulosic membranes (12), nevertheless, given the present distaste for any extractible additive, it was decided to establish quantitatively the extraction of this compound. This was done by passing water through the filter and analyzing the glycerol in the filtrate (13). A single disk 293 mm in diameter was placed in a stainless steel housing of an improved design which minimzed the holdup of the product side of the filter (14). This large disk was chosen both because it contained an amount of glycerol sufficient for analysis (~0.075 g/disk) and because the information is of practical interest since this is the size which is most commonly utilized for production processing of fluids. One liter of deionized water was passed through the membrane and successive portions of the eluate were collected, concentrated almost to dryness on a hot plate and oxidized by the addition of periodic acid. Potassium iodide was then added and the liberated iodine titrated with sodium thiosulfate solution. The extraction curve demonstrates that the removal of glycerol is both rapid and quantitative, see FIG. 6. Approximately 90% of the glycerol is extracted by the first 50 ml and 95% by the second 50 ml of water to pass through the membrane. In other words, the passage of a column of water less than 2 mm in depth through the membrane will suffice to purge it of virtually all of its glycerol.

Morphology

Membrane morphology was studied with the aid of scanning electron microscopy (SEM). Considerable variability was found in both gross and fine structure. Both surfaces of each of the two noncellulosic membranes exhibit a lower effective pore density than do the surfaces of the M/E membranes. The noncellulosic membranes also exhibit a number of other structural peculiarities. Although both possess a similar "taffy-like" fine structure, a cross-sectional view of the polyamide membrane proved that is it comprised of two discrete (but apparently equivalent) layers, whereas the cross sectional view of the poly(vinylidene fluoride) membrane shows it to be a fiber-reinforced single layer, a feature which increases strength, but often adversely affects permeability and throughput (16). The pore size distribution of the poly(vinylidene fluoride) membrane is extremely broad, and the surface structure is characterized by the presence of structural irregularities and streaks some of which are visible to the naked eye. Furthermore, the poly(vinylidene fluoride) membrane is light tan when dry and becomes almost brown when wet. This is the result of a surface modification which was effected to induce wettability, since the hydrophobic version of this membrane is opaque white (1). In addition, the cell walls of both types are comprised of comparatively massive struts suggestive of low void volume and high resistance which is, of course, consistent with their rather modest flow characteristics. Close inspection of the cross sectional view of the polyamide membrane showed a separation which occurred between the two layers during preparation of the sample for SEM. Manipulation of additional samples proved that the two layers were separable even at room temperature.

Figure 7:
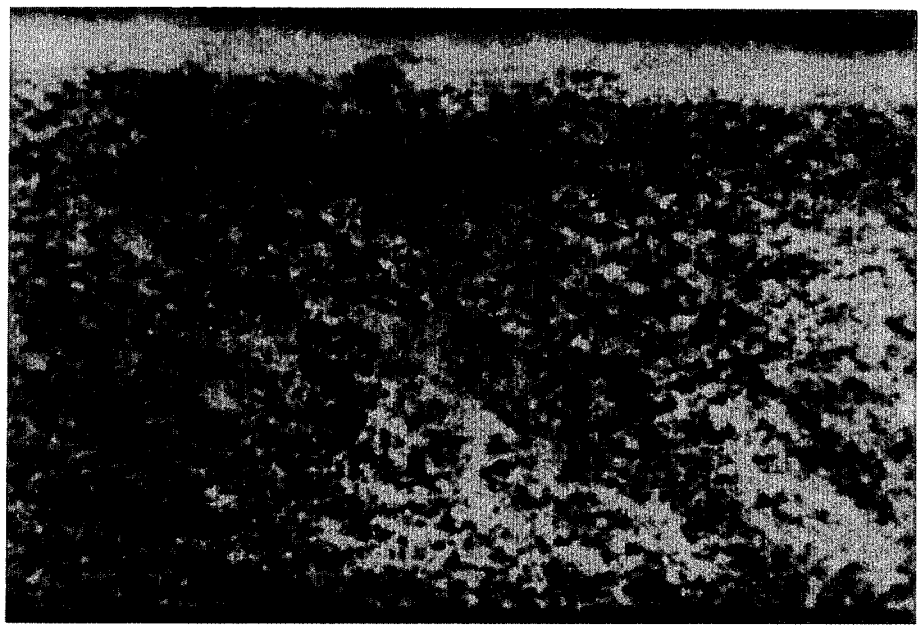
FIG. 7 is a scanning electron microscope photomicrograph of a cross-section of a "conventional" slightly anisotropic Millipore Type HC M/E membrane.

Both surfaces of the conventional M/E membrane are quite similar in appearance, and the cross section is only slightly an isotropic with little difference in pore and cell size from one surface to the other, see FIG. 7.

Figure 8:
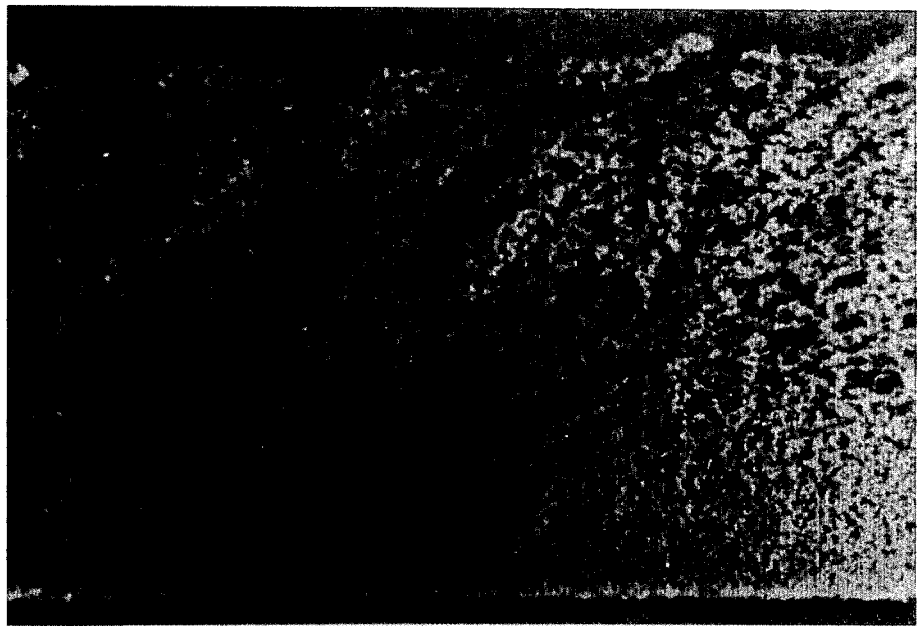
FIG. 8 is a scanning electron microscope photomicrograph of a cross-section, through the membrane, of a 0.45 μm Tyrann M/E membrane of this invention, showing the anisotropy through the membrane, top, as formed, up.

In contrast, a considerable difference was clearly apparent between the pore sizes at opposite surfaces of the Tyrann-M/E membrane (see FIG. 8). The structure is highly anisotropic with approximately five-fold difference between the size of the pores at the two surfaces. The same degree of anisotropy is found over the entire pore size range of Tyrann-M/E microfilters. Cross-sectional views indicated the presence of two integral (and, hence, inseparable) layers, the thicker of which contains the larger cells. This gradation in pore size from one surface to the other confers the filtration capacity of a prefilter/filter combination upon these integral bilayers.

The effects of anisotropy have been considered by earlier workers (5,16), and Pall et al. recognized the advantages of anisotropic fiber filters, but Tyrann-M/E represents a higher degree of anisotropy than previously obtained for any true phase inversion microporous polymer membrane. Although significant differences obviously exist between the structure of Tyrann-M/E and conventional M/E membranes, they are clearly more closely related to one another than to either of the noncellulosic membranes. Most importantly, M/E membranes exhibit a characteristically higher void volume and, hence, lower resistance than the noncellulosic types, see Table 6. The reason for this is probably related to the greater solubility of M/E polymers relative to that of the noncellulosic (15,17,18). Good solubility, it is believed, confers on a solution the tolerance for high concentrations of nonsolvents or swelling agents, the "pore-producing" constituents of the solutions from which membranes are cast. Since the ratio of the volumes of these pore-producing constituents to the volume of membrane polymer is proportional to void volume, it follows from my results that attainable void volume should also be proportional to polymer solubility.

TABLE 6

Void and Polymer Volumes For Survey Membranes

| Membrane | Specific Gravity of Dense Film (g/cc) | Pore Size (μm) | Void Volume (Porosity) (%) | Polymer Volume (100-Void Volume) (%) |
|---|---|---|---|---|
| Tyrann-M/E | 1.58 | 0.2 | 74.7 | 25.3 |
|  |  | 0.45 | 79.9 | 20.1 |
|  |  | 0.8 | 84.5 | 15.5 |
| Conventional-M/E | 1.58 | 0.2 | 74.4 | 25.6 |
|  |  | 0.45 | 79.3 | 20.7 |
|  |  | 0.8 | 83.0 | 17.0 |
| Polyamide | 1.14 | 0.2 | 73.6 | 26.4 |
|  |  | 0.45 | 75.2 | 24.8 |
| Poly(vinylidene Fluoride) | 1.75 | 0.2 | 72.2 | 27.8 |
|  |  | 0.45 | 73.8*(68.1) | 26.2*(31.9) |

*Estimate only since fiber reinforcement made experimentally determined value (in parenthesis) uncertain.

Subtle differences are also apparent between the fine structures of conventional M/E and Tyrann M/E membranes. The former appears to consist of a structure reminiscent of jumbled jacks. The latter contains longer strands somewhat like a mat of spaghetti. Although there is no proof that in this instance differences in microcrystalline habit are responsible for observable differences in SEM fine structure, it is tempting to speculate that the "jacks" indicate the presence of lamellar microcrystallites and the "spaghetti" structure, a more extended chain type of microcrystallite. The latter would be consistent with the greater elasticity, and hence flexibility, of Tyrann-M/E.

MECHANICAL AND THERMAL PROPERTIES

Although Tyrann-M/E and conventional M/E membranes are superior to the new polyamide and poly(vinylidene fluoride) membranes with respect to flow rates and filtration capacities, the latter are more suitable for filtration of most (but not all) organic solvents and, partially as a result of their lower void-(and higher polymer)-volumes, see Table 5, exhibit mechanical and thermal properties which are generally superior to those of the cellulosics. It should also be noted that in the special case of fiber-reinforced membranes, the mechanical properties are predominantly functions of the embedded fibers rather than of the membrane structure per se.

Considerable differences are apparent between the flexibility and autoclavability of Tyrann-M/E and conventional M/E membranes, see Tables 5 and 6. The former are considerably more flexible. This characteristic flexibility has the advantage that it virtually eliminates breakages in normal handling of flat stock membranes, a nemesis of the conventional M/E type.

Figure 9:
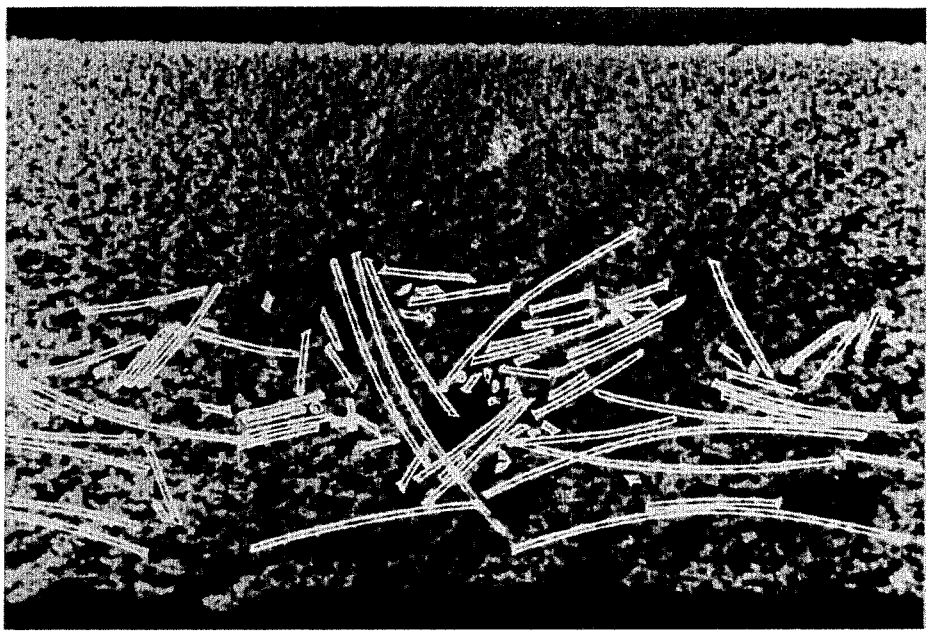
FIG. 9 is a modified scanning electron microscope photomicrograph of a cross-section of a 0.45 μm Tyrann M/E membrane with an added showing of the location of reinforcing fibers according to one species of this invention, top, as formed, up.

Strength, toughness and dimensional stability are increased without significant impairment of filtration characteristics by casting the membrane of a fiber reinforcement. Woven fibers, random loose fibers or non-woven fabric may be used. Non-woven polyester fabric is preferred and is schematically depicted in the membrane of FIG. 9, wherein the fabric is mainly in the coarse portion of the membrane.

machine direction ($\geq 8\%$) below which any membrane cannot be sharply creased without fracturing. Conventional M/E membranes exhibit an elongation at break of approximately 5% and literally burst into shreds when the break point has been reached whereas the more elastic Tyrann-M/E membrances break normally. It may be that a portion of the flexibility of Tyrann-M/E is due to its spaghetti-like fine structure. It is highly significant that Tyrann-M/E can be creased in the anhydrous condition and that the integrity of the membrane along the fold is maintained as evidenced by the constancy of bubble points after flexing before and after both wet and dry autoclaving. This behavior is in sharp constrast with that of conventional M/E membranes which, although they can, when wet, be bubble pointed along a fold before (but not after) wet autoclaving, cannot when dry be bubble pointed across any fold because of their extreme friability. A further peculiarity of conventional M/E membranes is that autoclaving produces uneven shrinkage between machine and transverse directions with the result that a disk which is circular before autoclaving becomes elliptical after autoclaving (Table 8). Tyrann-M/E, on the other hand, experiences less extensive and more uniform shrinkage and a less severe drop in permeability. The change in bubble points for both membrane types as a result of autoclaving is insignificant. Although the origin of the profound differences in mechanical and thermal properties of Tyrann-M/E and conventional M/E membranes is as yet incompletley understood, it may be related to previously noted differences in fine structure, i.e., to a more extended chain configuration in the former. On the other hand, differences in the type and concentration of the wetting agents may also be partially responsible.

TABLE 7

Effects of Flexing* and Autoclaving** Upon the Bubble Points of Water-Wet 0.45 μm M/E Membranes

| M/E Membrane Type | Autoclaving Condition | Bubble Point (psi) | | |
|---|---|---|---|---|
| | | (Initial) | (Flexed Before Autoclaving) | (Flexed After Autoclaving) |
| Tyrann- | Dry, unrestrained | 34.6 ± 0.3 | 34.5 ± 0.2 | 34.0 ± 1.0 |
| Tyrann- | Wet, restrained | 34.7 ± 1.3 | 34.5 ± 0.3 | 36.8 ± 0.5 |
| Conventional | Dry, unrestrained | 35.7 ± 1.1 | Failed+ | Failed+ |
| Conventional | Wet, restrained | 36.1 ± 0.8 | 35.9 ± 0.8 | Failed+ |

*Flexing = a double sharp fold along the diameter of a circular 47 mm disk.
**All samples autoclaved at 121° C. for 15 minutes.
+Bubble point too low to measure owing to catastrophic loss of membrane integrity.

TABLE 8

The Effects of Dry* Autoclaving Upon the Diameters, Ellipticites,** and Air Flow Rates of Various 0.45 μm Membranes

| Membranes | Decrease In Diameter After Dry Autoclaving* (%) | Ellipticity** (%) | Air Flow Rate After Dry Autoclaving* ($1 \min^{-1} cm^{-2}$) at 10 psi | Decline In Air Flow Rate After Dry Autoclaving* (%) |
|---|---|---|---|---|
| Tyrann-M/E | 3.2 ± 0.4 | ±0.1 | 9.80 ± 0.05 | −8 |
| Conventional M/E | 6.0 ± 1.4 | ±1.4 | 5.05 ± 0.12 | −18 |
| Polyamide | 1.4 ± 0.3 | ±0.1 | 3.65 ± 0.04 | −2 |
| Poly(Vinylidene Fluoride) | 0.2 ± 0.3 | ±0.3 | 3.65 ± 0.23 | −0.5 |

*Dry autoclaving, unrestrained, 121° C., 15 min. (Membrane dry when placed in the autoclave.)
**Inasmuch as all samples were perfectly round 47 mm disks before dry autoclaving, the standard deviation of the measured diameters after autoclaving is a measure of ellipticity, i.e., uneven shrinkage in machine and transverse directions.

A mechanical property which appears to be related to flexibility is elongation at break. There appears to exist a threshold value of elongation at break in the

SUMMARY

Tyrann-M/E, a new class of M/E membranes whose gross morphology is characterized by anisotropy, i.e., a gradation of pore and cell size from one surface to the other have been developed. Conventional M/E and noncellulosic membranes are isotropic or only slightly anisotropic, whereas Tyrann-M/E is highly anisotropic, consisting of an integral bilayer, two-thirds of which is represented by cells approximately five times larger than those found in the remaining one-third. Anisotropy is characteristic of the entire range of Tyrann-M/E microfilters encompassing 0.1, 0.2, 0.45 and 0.8 μm pore sizes. By positioning the membrane such that the larger-pored surface is in contact with the feed solution, both product rate and filtration capacity are substantially greater than those obtained for conventional isotropic membranes. That this increased throughput has been accomplished without the loss of sterilization efficiency is demonstrated through the successful passage of stringent bacterial challenge tests by 0.2 and 0.45 μm Tyrann-M/E. Its high degree of anisotropy, furthermore, may enable 0.45 μm Tyrann-M/E to serve as an efficient "cradle" to maximize bacterial recovery in water analysis applications.

In contrast to the filtration capacity which is a function of gross morphology, the physical properties of M/E membranes, such as elasticity and flexibility, appear to vary with the nature of cellular fine texture. The "jumbled jack" configuration found in conventional M/E membranes may indicate the presence of lamellar microcrystallites and be responsibe for their friability. Tyrann-M/E membranes, on the other hand, exhibit a "spaghetti" texture which is not inconsistent with the presence of extended chain microcrystallites and, perhaps as a result, are quite flexible. Thermal stability (lesser and more uniform shrinkage during autoclaving) is also greater for Tyrann-M/E than for conventional M/E membranes.

In summary, Tyrann-M/E represents a new highly anisotropic class of membrane filter with permeability and dirt holding characteristics which are superior to those of both noncellulosic and conventional M/E membranes and with flexibility and thermal stability which are significantly greater than those of conventional M/E membranes.

INDUSTRIAL APPLICATION

The membranes of this invention find wide industrial application in laboratory and industrial filtration of liquids, bacterial sterilization, and microfiltration generally and in general clinical and scientific laboratory testing, diagnostic procedures, and developmental procedures.

REFERENCES CITED IN TEXT

1. M. Accomozzo, paper presented at the Filtration Society Conference in Monterey, CA, February 1980.
2. F. Nordhauser, ibid.
3. Difco Manual Ninth Edition, P. 256, 1974.
4. Standard Methods for the Examination of Water and Wastewater, Procedure 909A, Fourteenth Edition American Public Health Association, Washington, D.C., 1976.
5. K. Sladek, R. Suslavich, B. Sohn, and F. Dawson, paper presented at the Symposium on the Recovery of Indicator Organisms Employing Membrane Filters, sponsored by EPA and ASTM (Committee D-19 on Water), 1977.
6. T. Melzer and T. Meyers, Bull. Parenter. Drug Assoc. 25, 165 (1971).
7. D. Pall, Bull. Parenter, Drug Assoc., 29, 192 (1975).
8. K. Wallhäusser, Pharm. Ind., 36, (12) 931 (1974); 37 (1), 10 (1975).
9. A. Baszkin, D. Lyman and T. Meltzer, Pharmaceutical Technology, January 1979.
10. R. Kesting, W. Subcasky, and J. Paton, J. Colloid Interface Sci., 28, 156 (1968).
11. R. Kesting and W. Subcasky, J. Macromol. Sci. A3 (1), 151 (1969).
12. D. Mehta, D. Hauk, and T. Meltzer, paper presented at the Second World Filtration Congress, London, England (1979).
13. S. Siggia and G. Hanna, Quantitative Organic Analysis Via Functional Groups, Fourth Edition, Wiley-Interscience, New York (1979).
14. Creative Scientific Equipment Corp., Long Beach, Calif.
15. R. Kesting, Synthetic Polymeric Membranes, McGraw-Hill, New York (1971).
16. J. Marshall and T. Meltzer, Bull. Parenter, Drug Assoc., 30, (5), 214 (1976).
17. R. Kesting in Reverse Osmosis and Synthetic Membranes, S. Sourirajan, ed., National Research Council, Canada Publ. No. 15627 (1977).
18. R. Kesting, Pure & Appl. Chem., 50, 633 (1978).

What is claimed is:

1. A method of manufacturing microporous polymeric membranes comprising the steps of:
    forming a casting solution consisting essentially of a solvent, a non-solvent and polymer, the solvent being selected from the group consisting of methyl formate, propylene oxide or mixtures thereof, the non-solvent consisting essentially of isopropyl alcohol, t-butyl alcohol or a mixture of said alcohols, and the polymer being selected from the group consisting of cellulose nitrate and mixtures of cellulose nitrate and cellulose acetate, cellulose nitrate content exceeding cellulose acetate content therein;
    casting said solution onto a substrate; and
    allowing the solvent and the non-solvent, respectively, to evaporate to thereby form an anisotropic cellulosic membrane having a first pore size adjacent one surface and a second smaller pore size adjacent the other surface of the membrane.

2. A process for forming an anisotropic polymeric microfiltration membrane consisting essentially of the steps:
    (a) preparing a solution consisting essentially of a polymer selected from the group consisting of cellulose nitrate and mixtures of cellulose acetate and cellulose nitrate, cellulose nitrate content exceeding cellulose acetate content therein, in an amount of from about 0.1 percent to about 10 percent by weight of the solution, a solvent for the polymer selected from the group consisting of methyl formate and propylene oxide and mixtures thereof, and isopropyl alcohol, t-butyl alcohol or a mixture of said alcohols as a non-solvent;
    (b) casting the solution to form a thin layer of said solution; and
    (c) allowing the solvent and the non-solvent to evaporate completely, thereby forming said membrane by a dry phase inversion process.

3. The process of claim 2 further including the step of providing a layer of fibers and then casting said solution over said layer of fibers to form a thin layer which includes therein said fibers, the fibers then forming reinforcing for the resultant membrane.

4. The process of claim 2 including the step of including in the casting solution an amount of glycerol, effective to impart flexibility to the resulting membrane, said glycerol remaining as a leachable component of the resulting membrane.

5. The process of claim 4 including the additional step of leaching the glycerol from the membrane to provide a membrane free of leachable constituents.

6. The process of claim 4 further including the step of providing a layer of fibers and then casting said solution over said layer of fibers to form a thin layer which includes therein said fibers, the fibers then forming reinforcing for the resultant membrane.

7. In the manufacture of microporous polymeric membranes by the dry phase inversion process in which a casting solution of predetermined composition is prepared, cast and dried to form a membrane, the improvement wherein the step of preparing the casting solution comprises preparing a casting solution in which the solvent consists essentially of methyl formate or propylene oxide, a non-solvent selected from the group consisting of isopropyl alcohol, t-butyl alcohol and mixtures of said alcohols, and cellulose nitrate or cellulose nitrate - cellulose acetate mixed ester, cellulose nitrate content exceeding cellulose acetate content therein, as the polymer.

8. In the manufacture of microporous polymeric membranes by the dry phase inversion process in which a casting solution of predetermined composition is prepared, cast and dried to form a membrane, the improvement wherein the step of preparing the casting solution comprises preparing a casting solution in which the solvent consists essentially of propylene oxide, a non-solvent selected from the group consisting of isopropyl alcohol, t-butyl alcohol and mixtures of said alcohols, and cellulose nitrate or cellulose nitrate - cellulose acetate mixed ester, cellulose nitrate content exceeding cellulose acetate content therein, as the polymer.

* * * * *